(12) United States Patent
Leroux et al.

(10) Patent No.: US 7,691,408 B2
(45) Date of Patent: Apr. 6, 2010

(54) COMPOSITION HAVING GELLING PROPERTIES FOR THE PROLONGED DELIVERY OF BIOACTIVE SUBSTANCES

(75) Inventors: Jean-Christophe Leroux, Montreal (CA); Anne-Claude Couffin-Hoarau, Montreal (CA)

(73) Assignees: Ethypharm, Houdan (FR); Universite De Montreal, Montreal (CA)

( * ) Notice: Subject to any disclaimer, the term of this patent is extended or adjusted under 35 U.S.C. 154(b) by 775 days.

(21) Appl. No.: 10/507,281

(22) PCT Filed: Mar. 12, 2003

(86) PCT No.: PCT/FR03/00797

§ 371 (c)(1),
(2), (4) Date: Jun. 9, 2005

(87) PCT Pub. No.: WO03/075885

PCT Pub. Date: Sep. 18, 2003

(65) Prior Publication Data

US 2006/0121115 A1 Jun. 8, 2006

Related U.S. Application Data

(60) Provisional application No. 60/405,720, filed on Aug. 26, 2002.

(30) Foreign Application Priority Data

Mar. 12, 2002 (FR) .................................. 02 03059

(51) Int. Cl.
*A61K 9/14* (2006.01)
*A61K 9/54* (2006.01)
(52) U.S. Cl. ...................... 424/458; 424/486
(58) Field of Classification Search .................. 424/458, 424/486
See application file for complete search history.

(56) References Cited

U.S. PATENT DOCUMENTS

| | | | |
|---|---|---|---|
| 3,932,624 A | 1/1976 | Fulton | |
| 3,969,087 A | 7/1976 | Saito et al. | |
| 5,575,815 A | 11/1996 | Slepian et al. | |
| 5,843,407 A * | 12/1998 | El-Nokaly et al. | ............ 424/64 |
| 6,306,383 B1 | 10/2001 | Crandall | |
| 6,344,488 B1 | 2/2002 | Chenite et al. | |
| 6,464,987 B1 | 10/2002 | Fanara et al. | |
| 6,471,970 B1 | 10/2002 | Fanara et al. | |
| 2001/0007673 A1 | 7/2001 | Goldenberg et al. | |

FOREIGN PATENT DOCUMENTS

| | | |
|---|---|---|
| EP | 1 063 007 A1 | 12/2000 |
| WO | 94/08623 A1 | 4/1994 |
| WO | 97/15287 A1 | 5/1997 |
| WO | 99/13913 A2 | 3/1999 |
| WO | 03/075885 A1 | 9/2003 |

OTHER PUBLICATIONS

Luo et al., *Chem. Commun*, 2001, pp. 1556-1557, published by Royal Society of Chemistry, Cambridge, UK.
Bhattacharya et al., *Chem Commun*., 2001, pp. 185-186, published by Royal Society of Chemistry, Cambridge, UK.
Murdan et al., *Journal of Pharmaceutical Sciences*, vol. 88, No. 6, Jun. 1999, pp. 608-614, published by American Pharmaceutical Assn. & Wiley, Easton, PA.
Willimann et al., *Journal of Pharmaceutical Sciences*, vol. 81, No. 9, Sep. 1992, pp. 871-874. published by American Pharmaceutical Assn. & Wiley, Easton, PA.
Johnston et al., *Journal of Parenteral Science & Technology*, vol. 43, No. 6, Nov.-Dec. 1989, pp. 279-286, published by Parenteral Drug Association, Bethesda, MD.
Johnston et al., *Pharmaceutical Research*, vol. 9, No. 3, 1992, pp. 425-434, published by Plenum Publishing Company, Stuttgart, Germany.
Pec et al., *Journal of Pharmaceutical Sciences*, vol. 81, No. 7, Jul. 1992, pp. 626-630, published by Plenum Publishing Company, Stuttgart, Germany.
Miyazaki et al., *Journal of Controlled Release*, 56, 1998 pp. 75-83, published by Elsevier Science Publishers, Amsterdam, Holland.
Couffin-Hoarau et al., *Pharmaceutical Research*, vol. 21, No. 3, Mar. 2004, pp. 454-457, published by Plenum Publishers, New York, New York.
Vintiloiu et al., "Organogels and their use in drug delivery—A Review," *J. Controlled Release*; vol. 125, (2008), pp. 179-192, Elsevier.

* cited by examiner

*Primary Examiner*—Robert A Wax
*Assistant Examiner*—Aradhana Sasan
(74) *Attorney, Agent, or Firm*—Buchanan, Ingersoll & Rooney, P.C.

(57) ABSTRACT

The invention relates to a heat-sensitive composition in liquid form, containing: an organic hydrophobic liquid; an organogelling substance, the molecules of which can be bound to one another by low energy linkages; and a bioactive substance, which switches to organogel form upon coming into contact with a physiological fluid during the administration thereof into an animal body, in particular, a human.

28 Claims, 9 Drawing Sheets

COMPOSITION HAVING GELLING PROPERTIES FOR THE PROLONGED DELIVERY OF BIOACTIVE SUBSTANCES

CROSS-REFERENCE TO RELATED APPLICATIONS

This application is the U.S. national stage of International Appln. No. PCT/FR03/00797, filed Mar. 12, 2003, which claims benefit under 35 U.S.C. §119(e) of U.S. Provisional Appln. No. 60/405,720, filed Aug. 26, 2002 and which also claims priority under 35 U.S.C. §119 of French Patent Application No. 02/03059, filed Mar. 12, 2002.

The present invention relates to a heat-sensitive chemical composition comprising a hydrophobic organic solvent, an "organogelling" substance and a bioactive substance, the said composition being intended to be administered to a living organism, for the sustained delivery of bioactive substances.

The said composition has the capacity to form an organogel spontaneously or by cooling, once placed in contact with an aqueous medium, and especially a physiological fluid. The said organogel formed serves as a support for the sustained release of bioactive substances by diffusion and/or erosion and/or gradual biodegradation of the said organogel in the body.

The present invention also covers the uses that may be made of this composition in the therapeutic field and more particularly in the field of the sustained delivery of bioactive substances.

The expression "heat-sensitive composition" means any composition capable of changing from the liquid state to the gel state as a function of the temperature, and the term "organogel" means any gel whose liquid phase is composed of an organic solvent.

Moreover, the expression "bioactive substance" means any substance that has the capacity to act on a living organism or its functioning so as to prevent, cure, relieve or improve the condition of the said organism.

The expression "hydrophobic, organic liquid" means an organic solvent or mixture of organic solvents whose molecules or parts of molecules have a certain level of repulsion towards water molecules. The expression "hydrophilic solvent" means a solvent whose molecules establish attraction interactions with water molecules.

Gels have been used for a long time in the industrial field for the properties imparted to them by their particular physical structure.

Specifically, they correspond to an intermediate state of matter since they are composed both of elements in solid form and of elements in liquid form. The solid elements form a three-dimensional structure or matrix, organized as a network of mutually interconnected molecules, this network immobilizing the elements present in liquid form.

Gels may be classified as a function of the type of bonds that link together the molecules of the solid phase, or as a function of the type of organic or aqueous solvent of which the liquid phase is composed.

"Hydrogels" are gels whose liquid phase is an aqueous phase, to distinguish them from "organogels" whose liquid phase is an organic phase.

Gels whose matrix consists of molecules linked together via covalent bonds are generally in a stable and irreversible state once formed. In contrast, gels whose solid matrix is obtained by bonds of low energy (such as hydrogen bonds or Van der Waals bonds especially) are generally reversible gels, i.e. they can change from the gel state to the liquid state as a function of the surrounding conditions (pH, temperature, ionic strength, etc.).

In the case of heat-sensitive gels, the temperature at which the change of state is observed is known as the transition temperature. In the particular case of systems showing hysteretic behaviour, the gel/liquid transition temperature is different from the liquid/gel transition temperature.

Thus, gels are especially used in the pharmaceutical industry for their retention capacity with respect to bioactive molecules, especially in the context of a transcutaneous administration of active substances.

This retention property has moreover been exploited for a use of gels as vectors for the sustained delivery of medicinal products.

Thus, U.S. Pat. No. 3,932,624 describes the use of a hydrogel intended for the delayed delivery of saralasine. In the said patent, the gel is prepared based on gelatin, which, diluted in a physiological saline solution containing the bioactive substance, becomes impregnated therewith to form a gelled structure that may be surgically implanted into the body subcutaneously. The implanted gel gradually releases the active substance it contains by gradual erosion of the said gel.

However, this type of use necessitates the in situ surgical implantation of a preformed gel. This operation thus remains both expensive and a limitation on the patient.

To overcome this drawback, hydrogels that form in situ have been developed.

Thus, recently, patent application US No. 20010007673 describes the use of an in vivo-formed hydrogel intended for the delayed delivery of bioactive molecules, especially proteins. A composition based on a hydrophilic polymer including alginate, on a multivalent metal ion and on the desired active substance is injected in liquid form and changes to gel form once implanted into the body. Furthermore, on account of the thixotropic nature of the composition in gel form, it is possible to inject the composition in gel form, for example using a syringe, by applying a certain amount of pressure, after which the composition returns to the gel form in the body. This hydrogel allows a delayed diffusion of the bioactive substance into the bodily fluids.

Moreover, U.S. Pat. No. 5,575,815 describes the intracavital, i.e. intra-arterial or intravenous, implantation of an aqueous liquid composition that is converted or viscosified into a hydrogel in vivo. The use of this gel for the incorporation of active substances is envisaged especially for angioplasty. The hydrogels used consist of polyether polymers.

U.S. Pat. No. 6,344,488 describes the temperature-controlled and pH-dependent formation of a gel, comprising a chitosan/organophosphate salt aqueous mixture. The addition: of a dibasic monophosphate salt of polyol or of sugar to aqueous chitosan solutions results in a temperature-controlled and pH-dependent gelation. The medicinal products are incorporated into the said gel before the gelation. The chitosan/organo-phosphate salt solutions are stored at low temperatures in solution form and gel in situ after subcutaneous, intraperitoneal or intramuscular injection following a temperature increase. The hydrogel thus formed may be used for the release of active principles.

Patent application WO 97/15287 describes a system and a method for the parenteral (intramuscular, intra-peritoneal or subcutaneous) administration of medicinal product in a biodegradable polymer matrix to a warm-blooded animal in liquid form, resulting in the formation of a deposition of gel, for the controlled release of the medicinal product. The liquid is an aqueous solution in which is dissolved or dispersed an effective amount of medicinal product contained in a biodegradable copolymer block matrix. The copolymer has an inverse gelation temperature below the body temperature of the animal into which it is administered and is made of a hydrophobic polymer block and a hydrophilic polymer block.

Other heat-gelling aqueous solutions are described in the literature. Among these are poloxamer solutions (Johnston, T. P. et al., Inulin disposition following intramuscular administration of an inulin/poloxamer gel matrix, J. Parent. Sci. Technol., vol. 43, 279, 1989; Johnston, T. P. et al., Sustained delivery of interleukin-2 from a poloxamer 407 gel matrix following intraperitoneal injection in mice, Pharm. Res. 9, 425, 1992; Pec et al., Biological activity of urease formulated in poloxamer 407 after intraperitoneal injection in the rat, J. Pharm. Sci., vol. 81, 626, 1992) and xyloglucan solutions (Miyazaki, S. et al., Thermally reversible xyloglucan gels as vehicles for rectal drug delivery, J. Controlled Release, vol. 56, 75, 1998).

However, the main drawback of these hydrogels lies in their poor efficacy in terms of delivery of hydrophilic bioactive substances over long periods of time. This is due especially to their high proportion of water which gives them a high level of porosity, leading the hydrophilic bioactive substances present in such gels to be eliminated relatively quickly in the circulation. This phenomenon of diffusion is particularly important for very hydrophilic molecules of small size, for example such as certain hydrophilic medicinal products or certain hydrophilic peptides. The efficacy of the sustained release of these substances is therefore consequently reduced.

The object of the present invention is to provide a novel pharmaceutical composition that has the capacity to form an organogel allowing the release of active substances over long periods of time.

Furthermore, the object of the present invention is also to provide such a delayed-release support that is both biocompatible and biodegradable, also allowing it to be administered in liquid form, i.e. easily, quickly and inexpensively.

Organogels have already been used as a support for the delayed release of active principle.

The subject of the present invention is a hydrophobic organogel generated in vivo after having been applied in liquid form. Such gels have already been described in the prior art.

Patent application No. WO 94/08623 discloses a hydrophobic organogel containing lecithin and a solvent for the hydrophobic lecithin, which is used for the delayed release of protein. The gel forms in vivo, using a solution injected intramuscularly or subcutaneously, by absorption of water from the interstitial medium during injection.

In contrast, the hydrophobic organogel of the present invention is not formed by absorption of the surrounding water.

The present invention relates to a heat-sensitive liquid composition with gelling properties, comprising a hydrophobic organic liquid, an "organogelling" substance and a bioactive substance.

The organogelling substance consists of molecules capable of binding together via bonds of low energy to the extent that the self-assembly of these molecules is advantageously heat-reversible.

The heat-sensitive composition in liquid form according to the invention contains a hydrophobic organic liquid, an organogelling substance, the molecules of which have the capacity to bind together via bonds of low energy, and a bioactive substance. It changes to the organogel form when it comes into contact with a physiological fluid, during its administration into an animal body, in particular man, in particular during injection into the body, for example using a conventional syringe, via the extravascular parenteral or subcutaneous intramuscular route.

The expression "extravascular parenteral route" means any route of penetration into the body other than the digestive route and the vascular route (veins, arteries and blood vessels).

The composition of the invention may also be administered intraocularly, intracavitally or on prostheses prior to their application, vaginally, to an open wound or during surgery.

Many documents describe topical-use compositions containing lecithin-based organogels (see, for example, U.S. Pat. No. 6,306,383). Lecithin is a mixture of phospholipids of low molecular weight. Lecithins are amphoteric, soluble in alcohol and form an emulsion with water. Lecithin organogels have been described as vehicles that are useful for facilitating the penetration of low molecular weight molecules (H. Willimann, et al., "Organogel lécithine comme matrice pour le transport transdermique des médicaments [Lecithin organogel as a matrix for the transdermal transport of medicinal products]", J. Pharm. Sci., vol. 81, 1992). Lecithin organogels are obtained by adding a small amount of water to a solution of lecithin in organic solvents such as isopropyl palmitate or cyclooctane. In these documents, the water is added to form the desired gel so that the organogel is formed before it is applied to the skin.

In contrast, the organogels of the present invention are in liquid form when they are administered to a living organism, and take the form of a gel once they come into contact with a physiological fluid. Moreover, lecithins do not constitute organogelling substances as defined in the context of the present invention.

The expression "physiological fluid" means any fluid circulating in an animal body such as, for example, lymphatic fluid, lachrymal fluid, cerebrospinal fluid, amniotic fluid, parenteral fluid and blood.

The organogel formed from the composition according to the invention has capacities for retaining bioactive molecules and more particularly molecules less than 100 000 daltons in weight and of hydrophilic nature, enabling a release of the said molecules into the body over periods longer than 3 days to be envisaged.

Finally, the said organogel formed in the body from the composition according to the invention has the capacity to be eliminated slowly by gradual erosion and/or biodegradation, without toxicity to the body in which it is implanted.

This property of in situ gelation in accordance with the invention is obtained by using a hydrophobic organic liquid, constituting the organic phase of the said organogel, and via an organogelling substance, constituting the solid matrix of the said organogel.

The molecules constituting this organogelling substance are especially of the type such as fatty acid ester derivatives of amino acids, which have the capacity to self-assemble spontaneously to form a matrix that immobilizes the said hydrophobic organic liquid. This molecular self-assembly may be achieved by hydrogen bonds that become established between the groups of alcohol (—OH), acid (—COOH) and amine (—NH or $NH_2$) type borne by the organogelling molecules.

If necessary, the gelation of the liquid composition is induced by cooling the site of application of the composition or by diffusion of a hydrophilic organic solvent added to the composition of the invention.

The Applicant has selected hydrophilic organic solvents capable of creating weak bonds (e.g.: hydrogen bridges) with the molecules of organogelling substance, and capable of diffusing into aqueous media to produce the composition according to the invention.

Thus, the hydrophilic organic solvent introduced into the mixture forming the composition according to the invention will come into competition with the molecules of organogelling substance, creating with the said molecules weak bonds (e.g.: hydrogen bridges) that prevent the said molecules from self-assembling into a dense and unified network. The composition according to the invention will thus remain in liquid form for as long as the molecules of the said hydrophilic organic solvent remain bound to the organogelling molecules.

The use according to the present invention of the reversibility of the weak bonds will advantageously allow the organogelling matrix to become reassembled as soon as the said hydrophilic organic solvent has diffused into the surrounding medium.

Thus, as soon as it comes into contact with an aqueous solution and more particularly with physiological fluids such as interstitial fluid, lymph or intraperitoneal fluid, for example, the said hydrophilic organic solvent present in the composition in accordance with the invention will diffuse into the said surrounding fluid due to its hydrophilicity.

The diffusion of the said hydrophilic organic solvent will then allow the molecules of the said organogelling substance to self-assemble. By creating a structured network, this self-assembly will allow the said hydrophobic organic liquid to be retained, causing the said composition to change from the liquid state to the gel state.

The present invention thus offers a simple system for spontaneous in situ gelation and easy administration.

Moreover, the present invention is based on the hysteretic properties observed by the Applicant on organogels based on organogelling substances in accordance with the invention. The term "hysteresis" means the physical phenomenon observed especially for gellable compositions, representing the difference existing between the gel/liquid transition temperature and the liquid/gel transition temperature. Specifically, with these properties, a composition in accordance with the invention that is liquid, and thus readily injectable, at room temperature (or at a temperature in the region of room temperature) may be envisaged. Furthermore, with these properties, an organogel according to the invention may also be produced, which, once formed in vivo, will remain in gel form at the body temperature of the organism under consideration. The reason for this is that such an organogel, whether it is formed by diffusion or by simple cooling, has a gel/liquid transition temperature that is higher than the temperature of the site of injection or of application. Consequently, it is entirely stable in the said organism.

Finally, the present invention has the advantage of providing a support for the sustained release of medicinal products or other active substances. Specifically, the organogel formed in the organism and in accordance with the present invention comprises a veritable organized matrix structure that has little affinity for the surrounding aqueous medium, and thus allows a slow release of the active substance by gradual diffusion, erosion or biodegradation of the said organogel.

The present invention thus provides a simple, effective and easily administered support for sustained release into the body, over a period at least equal to 1 day, of substances such as bioactive substances and more particularly of molecules of hydrophilic nature weighing less than 100 000 daltons.

In addition, the composition according to the present invention has the advantage of being extremely inexpensive, both in terms of manufacture as is described later, and in terms of packaging and administration.

The organogelling substances in accordance with the invention are substances whose molecules have the capacity to bind together via bonds of low energy, and especially via hydrogen bonds, allowing the formation of a heat-sensitive matrix. These molecules are especially molecules of low molecular weight with acid (—COOH) or alcohol (—OH) or amine (—NH$_2$ or —NH) end groups, for example.

Moreover, these substances are preferentially biocompatible and do not give rise to metabolites that are toxic or hazardous to the body during their degradation by the said body.

Derivatives of amino acids or fatty acid ester derivatives of amino acids such as alanine, which not only display good biocompatibility and satisfactory organogelling power, but also mainly give the gelled system hysteretic properties, will preferably be used. These properties are reflected by a change from the liquid state to the gel state at a different temperature from that observed during the change from the gel form to the liquid form of the said composition. The Applicant has, to its credit, noted that the difference between these two transition temperatures varies as a function of the type of hydrophobic organic liquid used, and of the amount of organogelling substance used.

Thus, the Applicant has produced compositions in accordance with the invention whose transition temperatures and differences between these temperatures may be adjusted by simple modification of these two parameters. The results reflecting these variations are shown in FIGS. 1 to 7.

Preferably, the difference between these two transition temperatures is chosen such that the liquid/gel transition temperature is less than the body temperature of the living organism under consideration in the case where the organogel is administered without a hydrophilic organic solvent, and such that the gel/liquid transition temperature is higher than the abovementioned temperature.

Thus, alanine derivatives such as N-lauroyl-L-alanine acid (LA) or alanine ester derivatives such as N-lauroyl L-alanine methyl ester (LAM), N-lauroyl L-alanine ethyl ester (LAE), N-stearoyl L-alanine methyl ester (LAM) or N-stearoyl L-alanine ethyl ester (SAE) will preferably be used as the organogelling substance in accordance with the invention.

The amount of organogelling substance depends on the type of hydrophobic organic liquid to select for the organogel in accordance with the invention.

However, the proportion of this substance is advantageously chosen between 0.5 and 50% by weight relative to the total weight of the said composition.

The Applicant has found that the use as an organogelling substance of N-lauroyl-L-alanine methyl ester allows the said composition to change to the gelled state by simple cooling below the liquid/gel transition threshold and to remain in the gel state at a temperature above the liquid/gel transition temperature, in particular the temperature of the living organism.

Specifically, the Applicant has noted that the said organogel formed by cooling is stable in the range of temperatures between the liquid/gel transition temperature and the gel/liquid transition temperature.

This combination of observations led the Applicant to develop a heat-sensitive composition with gelling properties that have the capacity to change to gelled form by simple local cooling and to maintain this gelled state at the body temperature. In this particular case of the invention, the amount of hydrophilic organic solvent may be extremely small, or even zero since the gelation takes place by cooling the said composition rather than by diffusing the said hydrophilic organic solvent.

This embodiment is particularly advantageous since the presence of the hydrophilic organic solvent can be dispensed with, and thus the process for preparing the composition according to the invention can be further simplified and its cost price can also be reduced.

Thus, according to one particular embodiment, the heat-sensitive composition according to the invention contains a proportion of N-lauroyl-L-alanine methyl ester that is sufficient to allow the said composition to change from the liquid state to the organogel state by simple cooling of the said composition on contact with its site of injection into the body.

Such a cooling must be sufficient to cause the said composition, applied in liquid form, to change to its gelled form. This cooling, which may be performed by external application of a cold object such as an ice pack or a cold compress or any other cooling means around the site of injection, must allow a local cooling, to below the liquid/gel transition temperature of the said composition.

The composition according to the invention is thus preferably in liquid form at the temperature of the site of application, has a gel/liquid transition temperature that is higher than the body temperature and a liquid/gel transition temperature that is lower than the temperature of the organism under consideration or of the area into which the gel is implanted. Specifically, the skin temperature may be a few degrees lower than the general temperature of the organism.

In one preferred embodiment, the proportion of N-lauroyl-L-alanine methyl ester in the said composition is sufficient for the liquid/gel transition temperature to be below body temperature (37° C. in general) and for the gel/liquid transition temperature to be above body temperature (37° C. in general).

Even more preferably, the composition according to the invention must comprise a liquid/gel transition temperature of less than 30° C. and a gel/liquid transition temperature of greater than +35° C.

Thus, the composition according to the invention is preferably a composition whose range between the liquid/gel transition temperature and the gel/liquid transition temperature is advantageously at least 20° C., the liquid/gel transition temperature preferably being between +5° C. and +36° C.

The hydrophobic organic liquid of the composition according to the present invention is a hydrophobic organic solvent or a mixture of different hydrophobic organic solvents.

The mixtures of different hydrophobic organic solvents have the advantage of modifying the gelation profile or of facilitating the dissolution of certain bioactive substances.

The hydrophobic organic solvents that may be used to prepare the composition according to the present invention belong to the group of water-immiscible organic solvents capable of creating a structure of organogel type, in the presence of a sufficient amount of "organogelling." substance as described above.

These solvents are preferably biocompatible, i.e. tolerated by the host organism, and trigger little or no immune reaction, for example of inflammatory or allergic type.

Finally, it will be noted that it is preferable to use hydrophobic organic solvents that are liquid at room temperature, which simplifies the process for manufacturing and administering the composition in accordance with the invention.

Organic solvents that can be degraded slowly, i.e. not rapidly metabolized by the enzymes present at the site of injection, and especially by lipases, will preferably be used.

Thus, the, hydrophobic organic solvents in accordance with the invention belong to the group comprising plant oils, semi-synthetic oils and certain fatty acid esters, especially glycerol (in particular diglycerides and triglycerides).

It may thus be envisaged to use biocompatible plant oils such as soybean oil, corn oil, cottonseed oil, groundnut oil, olive oil, castor oil, sesame oil, almond oil or safflower oil for example.

A plant oil such as soybean oil with suitable gelling behaviour, slow biodegradability and excellent biocompatibility will preferably be used as hydrophobic organic solvent.

Among the fatty acid esters that may be used as hydrophobic organic solvents in accordance with the invention, examples that may be mentioned especially include ethyl oleate and isopropyl myristate.

More preferably, fatty acid esters of glycerol, especially triglycerides, will be used. Even more preferably, medium-chain (fewer than 18 carbon atoms) triglycerides such as Labrafac CC®, comprising two fatty acids of 8 and 10 carbon atoms, will be used.

Among the synthetic or semi-synthetic solvents that may be used as hydrophobic organic solvents in accordance with the present invention, mention may be made especially of squalene, benzyl benzoate, benzyl chloride and benzyl benzoate/benzyl alcohol mixtures or Crodamol® GTCC-PN.

Synthetic hydrophobic organic oils and solvents may also be combined.

According to the invention, the expression "hydrophilic organic solvent" means a solvent that has high affinity for aqueous media, i.e. that is water-miscible.

The type of hydrophilic organic solvent that may be used in the present invention is advantageously a solvent capable of acting as a destabilizer for the organogel, i.e. capable of creating weak bonds with the organogelling molecules. Such a solvent is moreover advantageously biocompatible, i.e. tolerated by the body, such that its diffusion results in little or no immune reaction of inflammatory or allergic type. A solvent that has undergone approval for parenteral use will thus preferably be used for the implementation of the present invention.

The said hydrophilic organic solvent in accordance with the invention will advantageously be used in proportions of less than 60% by weight of the said composition, and more preferably less than 20%.

Hydrophilic solvents that may be mentioned include solvents such as alcohols, for instance ethanol, glycerol, propylene glycol, poly(ethylene) glycol of low molecular weight, benzyl alcohol or chlorobutanol, and mixtures thereof. Moreover, other water-miscible solvents may be envisaged, such as dimethyl sulphoxide (DMSO), N-methylpyrrolidone, N,N-dimethylacetamide, furfural, glycerol formal, isopropylidene glycerol, ethyl lactate, acetic acid or lactic acid, and mixtures thereof.

These examples are not limiting, and it may be entirely envisaged to perform the invention using other hydrophilic organic compounds with gel-destabilizing properties, i.e. the capacity to create weak bonds with the organogelling substance in accordance with the invention.

The bioactive substances that may be released into the body from the organogel in accordance with the present invention are advantageously substances that are difficult to package for a sustained release, such as low molecular weight molecules of hydrophilic or very hydrophilic nature. Advantageously, the said bioactive substance will be used in proportions of from 0.5% to 70% by weight of the composition according to the invention.

Thus, the Applicant has tested the release from a preformed organogel of dextran molecules labelled with a fluorescent molecule: FITC (Fluoro-Iso Thio Cyanate).

Figure 1:
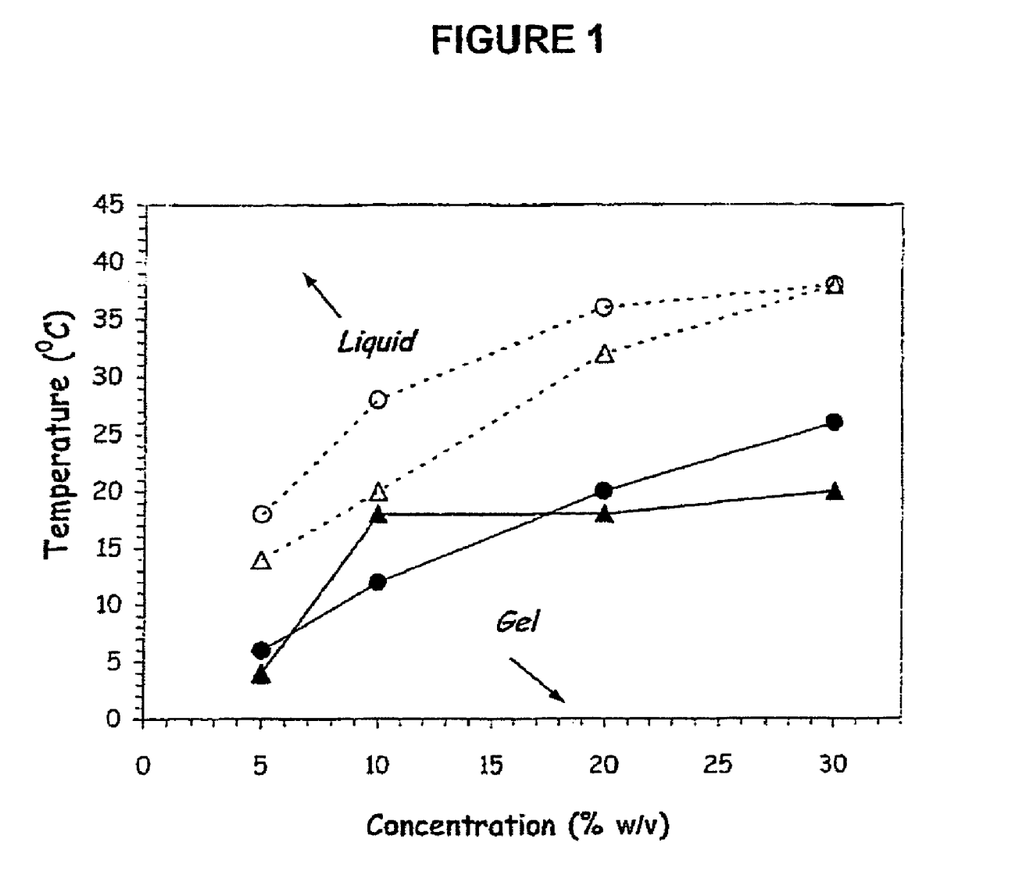
FIG. 1 is a diagram of the liquid-gel transition temperature (solid lines) and gel-liquid transition temperature (dotted lines) for N-lauroyl L-alanine methyl ester (LAM) in the presence of benzyl benzoate (circles) or of a benzyl benzoate/ 5% benzyl alcohol mixture (triangles).
Figure 2:
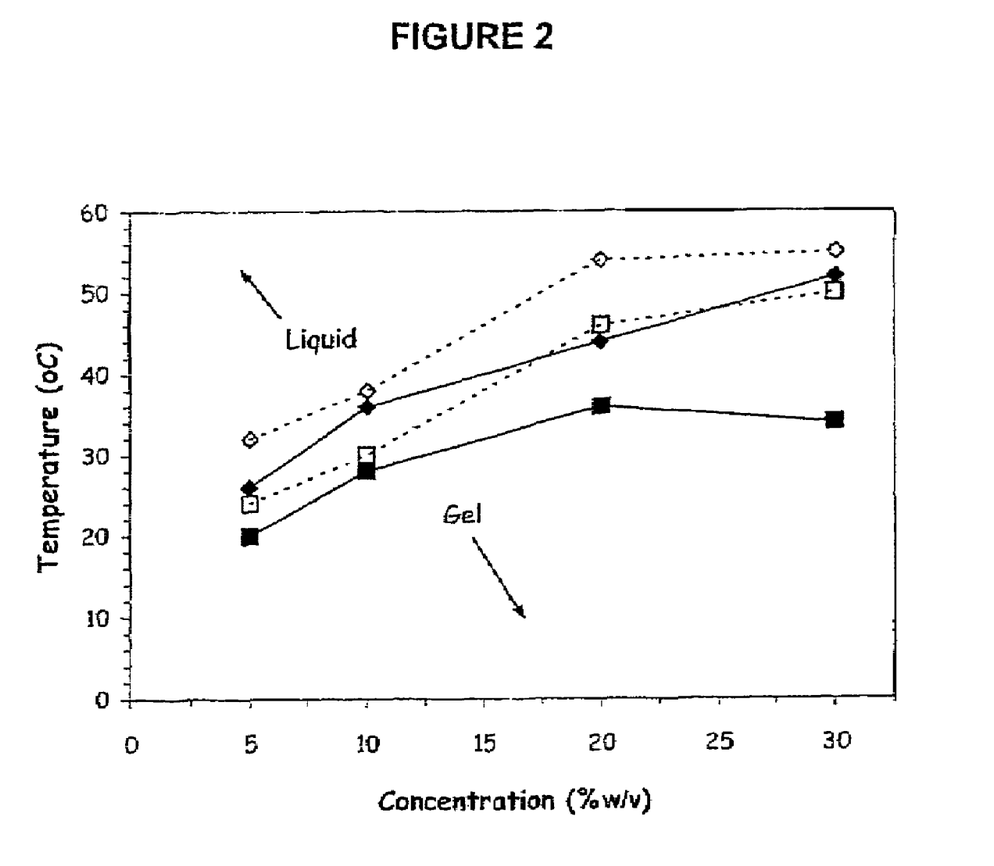
FIG. 2 is a diagram of the liquid-gel transition temperature (solid lines) and gel-liquid transition temperature (dotted lines) for LAM in the presence of soybean oil (diamonds) or of Labrafac® CC (squares).
Figure 3:
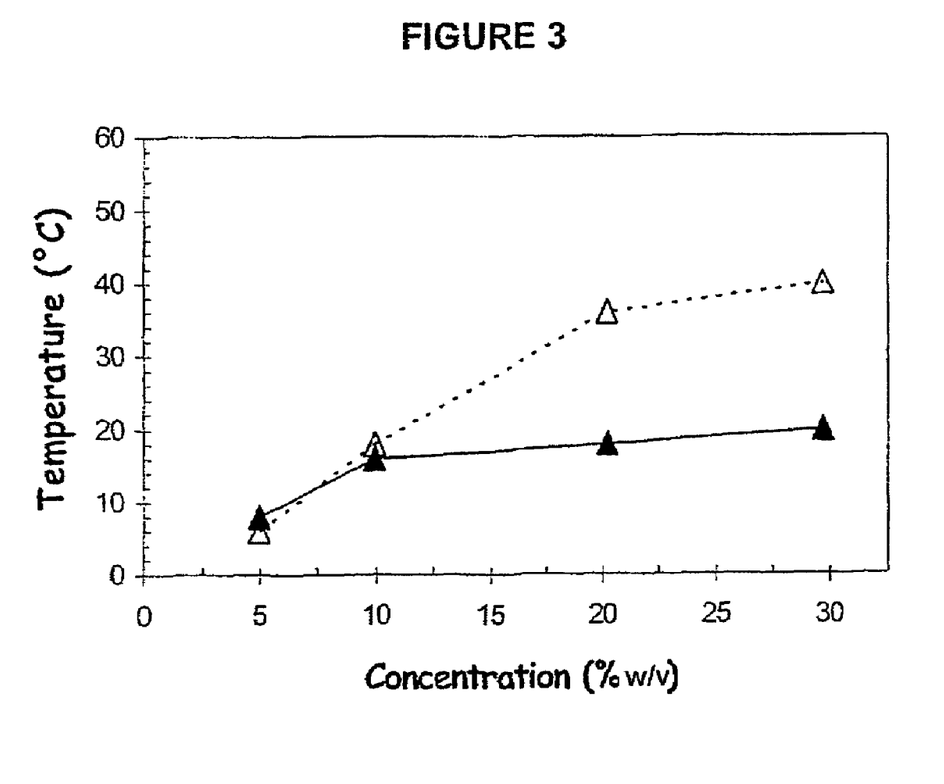
FIG. 3 is a diagram of the liquid-gel transition temperature (solid lines) and gel-liquid transition temperature (dotted lines) for N-lauroyl L-alanine ethyl ester (LAE) (triangles) in the presence of soybean oil.
Figure 4:
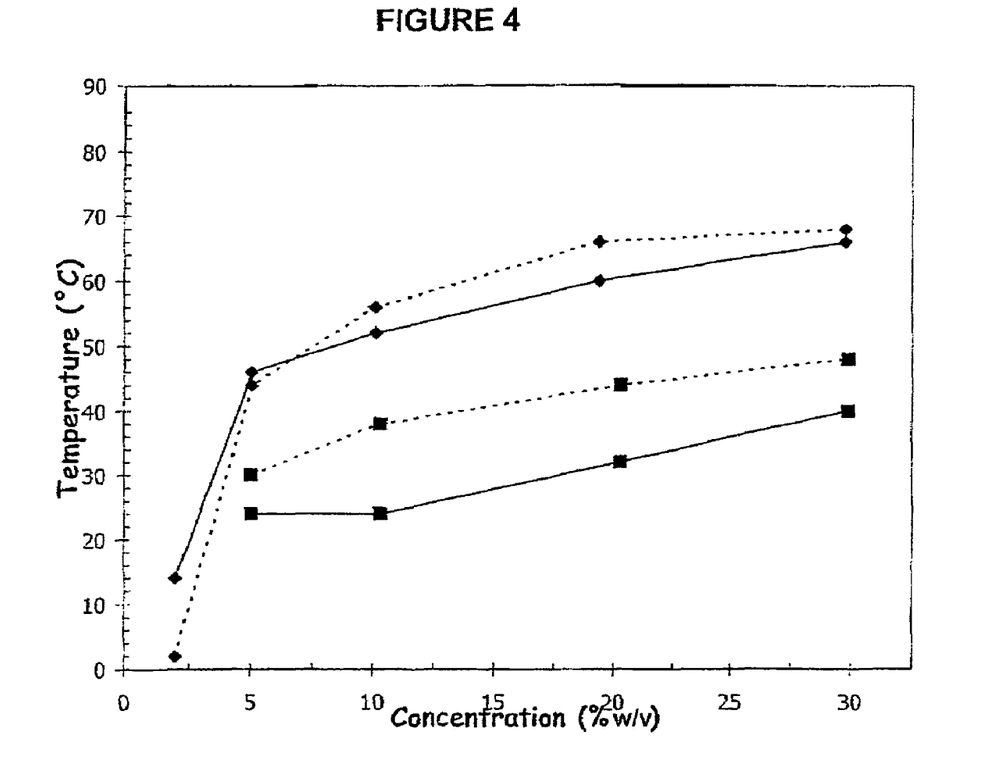
FIG. 4 is a diagram of the liquid-gel transition temperature (solid lines) and gel-liquid transition temperature (dotted lines) for LAM (squares) and for N-stearoyl L-alanine methyl ester (SAM) (diamonds) in the presence of ethyl oleate.
Figure 5:
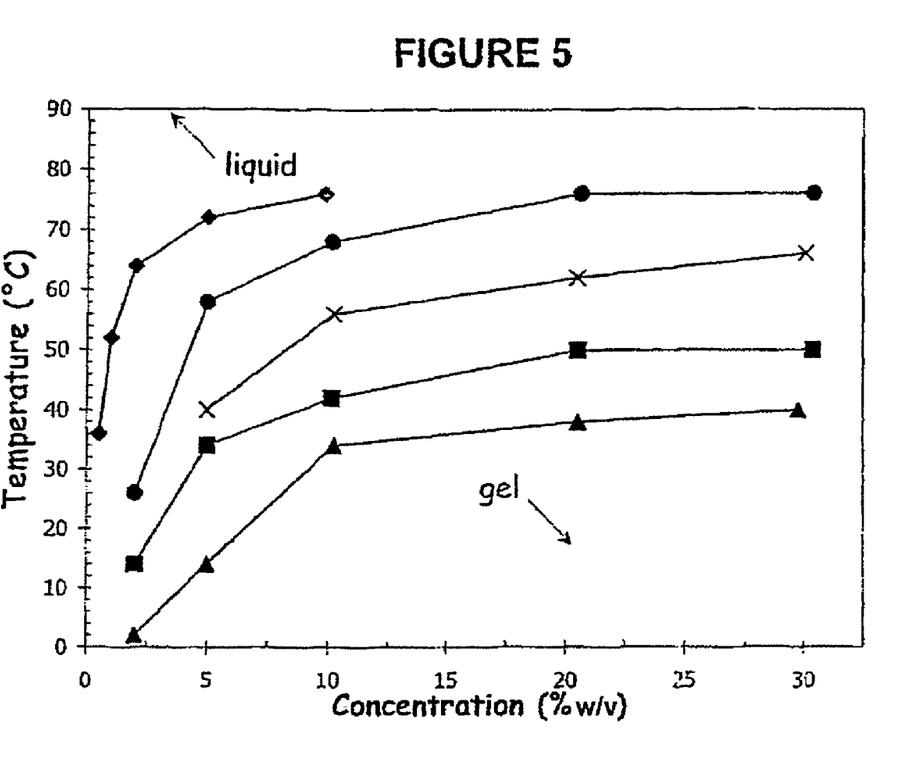
FIG. 5 is a diagram of the gel-liquid transition temperatures for LAM (squares), LAE (triangles), SAM (circles), N-stearoyl L-alanine ethyl ester (SAE) (crosses) and N-lauroyl L-alanine acid (LA) (diamonds) in maize oil.
Figure 6:
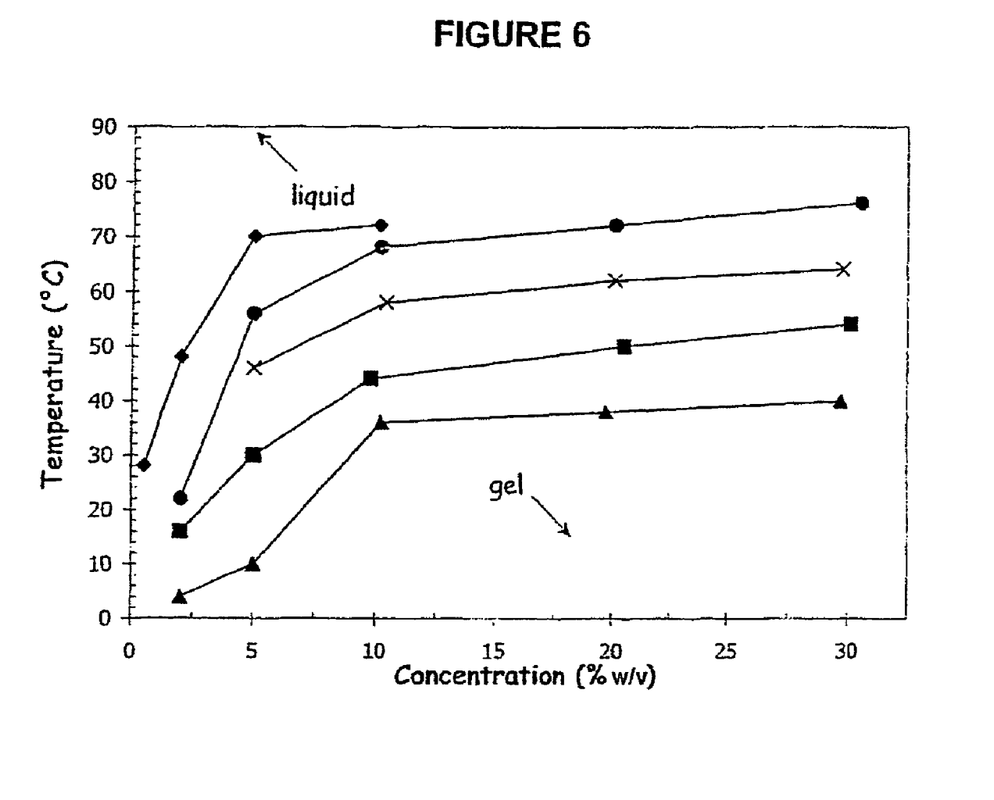
FIGS. 6 and 7 are diagrams of the gel-liquid transition temperatures for LAM (squares), LAE (triangles), SAM (circles), SAE (crosses) and LA (diamonds) in passionflower oil and Crodamol® GTCC-PN (triglycerides), respectively.
Figure 7:
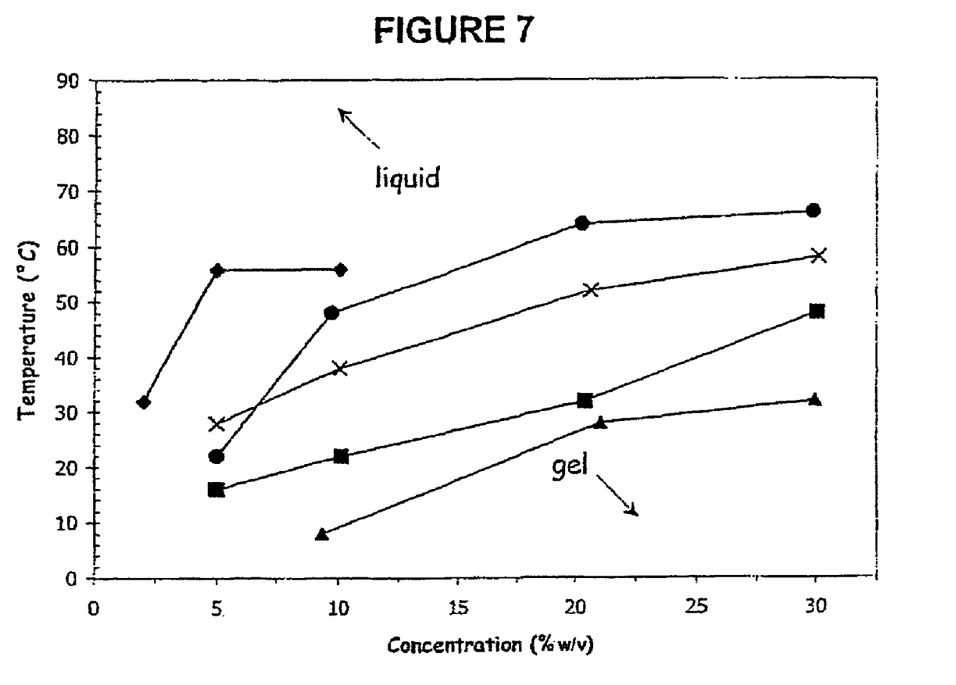
Figure 8:
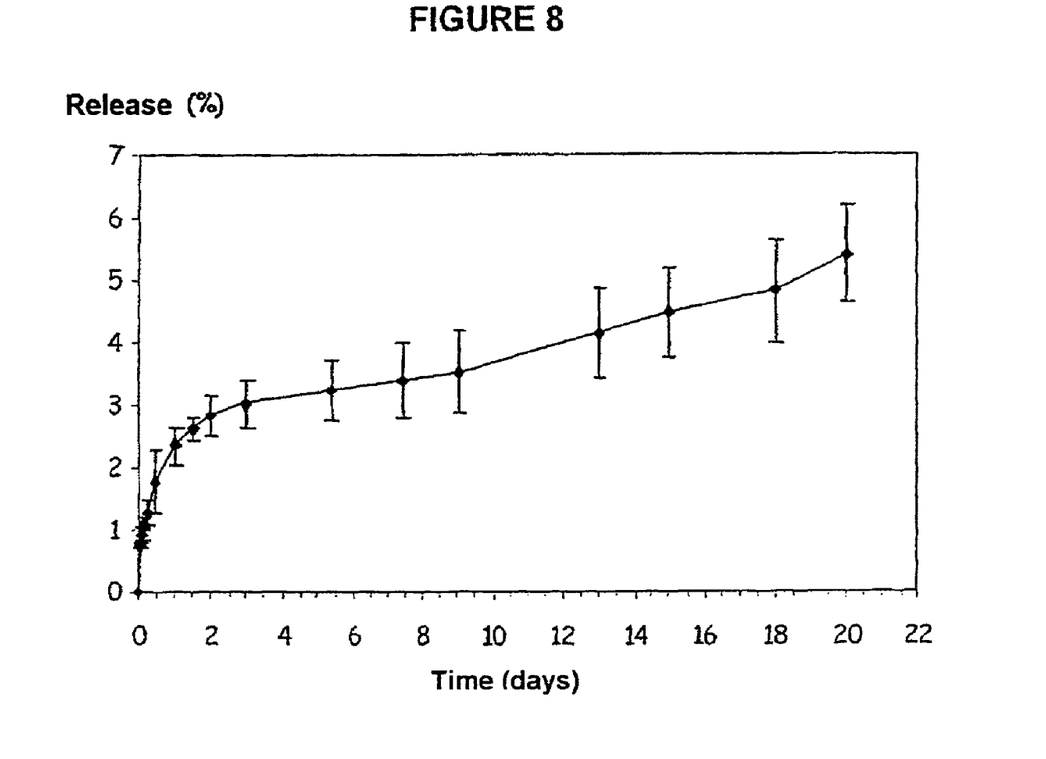
FIG. 8 is the monitoring over 20 days of the in vitro release profile of FITC-dextran (molecular weight=9500) from a gel consisting of soybean oil and 30% LAM in PBS at 37° C.

The release profile of the dextran was monitored in vitro over 20 days by assaying the fluorescence, as shown in FIG. 8. The fluorescence was measured by regular sampling of an aqueous solution of phosphate-buffered saline.

Thus, the release may be designed over periods of longer than 3 days for proteins especially of therapeutic interest, such as α-interferon, β-interferon, somatostatin, calcitonin, heparin, interleukins or erythropoietin, for peptides, amino acids or vitamins.

These examples are in no way limiting, and other types of molecules, in particular other proteins, may be entirely envisaged for such a sustained release from an organogel in accordance with the invention.

The release into the body, from the organogel according to the invention, of molecules such as certain hormones and especially certain peptide hormones such as human growth hormone, thyreotrope hormone or leuprolide, may thus be envisaged.

Thus, it may be envisaged to use the present invention for the sustained release into the body of nucleic acids, oligonucleotides or nucleic acid derivatives in particular.

Similarly, it may be entirely envisaged to perform the present invention with the aim of dissolving and then releasing, in a sustained manner, hydrophobic bioactive substances, i.e. substances with strong affinity for the organogel and weak affinity for the surrounding aqueous medium.

The present invention may thus be used for a large number of substances of therapeutic or medical interest for which a sustained release into the body is desired.

By way of example, the composition according to the present invention may be prepared in the following manner.

Case of a Diffusion-Gelling System

The organogelling agent is first dissolved spontaneously or by heating and/or stirring in the hydrophilic organic solvent.

Next, the active substance and the hydrophobic organic solvent(s) are incorporated into this mixture, and two cases may thus be presented:

a) Either the active substance is soluble in the organic phase thus formed:

In this case, the active substance is dissolved in the organic phase formed. The dissolution takes place spontaneously or by heating, with or without stirring.

In this case, it may also be envisaged to dissolve the said active substance directly into the hydrophobic organic solvent.

b) Or the active substance is sparingly soluble or insoluble in the organic phase:

In this case, the active substance may first be made "wet" by dispersing it in the organic phase formed by the hydrophilic organic solvent and the organogelling substance. After stirring, a suspension of active substance in the mixture is then formed. This suspension may then be added to the other constituents of the composition according to the present invention.

It is also possible to dissolve the active substance in a minimum amount of water. This aqueous solution of active substance will be added to the organic phase formed by the hydrophilic organic solvent and the organogelling substance. This aqueous phase is then emulsified in the organic phase by vigorous stirring. The more vigorous the stirring, the smaller the size of the aqueous particles formed in the organic suspension and the more stable the emulsion. This emulsion can then be used for the preparation of a composition in accordance with the invention.

It should be noted, however, that this technique using an emulsion has the advantage of keeping the complex molecules of active substance in an aqueous microenvironment, which greatly limits the disruptions to which they may be prone when they are subjected to the change of environment, in particular the possibilities of denaturing of the substance.

The hydrophobic organic liquid is then added to the mixture previously obtained, optionally with stirring and/or moderate heating until a uniform mixture is obtained.

This uniform mixture according to the invention can then be injected into a living organism via the extravascular parenteral route using a conventional syringe for subcutaneous injections. After a lag phase which depends on the formulation chosen, the formation of a hardened area is observed at the site of injection, which is proof of the in vivo formation of the organogel according to the invention.

If it is not surgically removed, the said organogel will, depending on its size and the nature of the components constituting it, be gradually biodegraded and/or eroded in the body over a longer or shorter period. This gradual biodegradation will result in the release of the active substance that may be contained in the organogel according to the invention.

It will preferably be chosen to produce such organogels whose biodegradation will take place over periods of longer than 3 days.

Case of a Cooling-Gelling System

In this case, the organogelling substance with hysteresis properties is first mixed with the hydrophobic organic liquid.

Next, the active substance is incorporated into this mixture. If the active substance is organosoluble, it will be dissolved in the mixture directly or with gentle stirring. When the active substance is sparingly organosoluble or not organosoluble, the said substance is dispersed, as previously, in the organic phase or a stable emulsion of active substance predissolved in water is prepared, as previously, in the organic phase formed.

The composition thus formed is stable and preferably liquid at room temperature. It is injected, for example, via the extravascular parenteral route.

Immediately after injection, a cold object (or any other cooling system) is held in contact with the site of injection long enough to allow the in situ gelation of the composition according to the present invention.

When the gelation is complete, the cooling system is removed. The site of injection then returns to the body temperature, the organogel according to the invention remaining stable at the said temperature.

The heat-sensitive composition with gelling properties in accordance with the invention may be used, for example, for the delayed delivery of bioactive substances over long periods, i.e. over periods of at least one day up to one week, generally more than 3 days. This composition may thus serve as a support for the delayed delivery of substances of any type, especially of substances of therapeutic or medical interest.

It may thus be envisaged to use the heat-sensitive composition in accordance with the invention for the delayed delivery of medicinal products that need to be kept at a constant level in the blood. This invention thus proves to be particularly advantageous for medicinal products ordinarily administered several times a day and intended to maintain an effective therapeutic level in the body.

It may thus be envisaged to use the invention for therapeutic substances such as morphine or medicinal products that act as regulators of the cardiovascular system or of the nervous system.

Similarly, it may be envisaged to use the composition according to the invention with the aim of overcoming certain deficiencies in the body, especially vitamin or hormone deficiencies. Thus, the present invention may serve as a support for the sustained delivery of hormones that need to be taken daily, and that are still currently administered by injection, which is a painful and restrictive mode of administration. On account of its easy administration, its harmlessness and its low cost, such a release support by organogel would eliminate these constraints for the patient.

This composition may also be used for the manufacture of a medicinal product intended to be injected into the body via the extravascular parenteral route and especially subcutaneously, intradermally, intraperitoneally or intramuscularly, intraocularly, intravascularly or vaginally, onto an open wound or during surgery.

It can, moreover, allow the manufacture of a medicinal product intended to be used as a vector for the sustained release of bioactive substance(s) into the body.

EXAMPLE 1

In Vivo Formation of an Organogel from a Composition in Accordance with the Invention This example seeks to confirm that the composition in accordance with the invention is indeed capable of gelling in vivo. The tests are performed on rats.

Soybean oil is used as hydrophobic organic solvent in accordance with the invention, and ethanol is used as hydrophilic organic solvent according to the invention.

The organogelling substance chosen is LAM (N-lauroyl-L-alanine methyl ester).

The proportions used are summarized in the following table:

| Product | Function | Proportion |
| --- | --- | --- |
| LAM | Organogelling agent | 20% w/v |
| Soybean oil | Hydrophobic organic solvent | qs 100 ml |
| Ethanol | Hydrophilic organic solvent | 14% v/v |

The organogelling agent is first dissolved in the ethanol. Next, the soybean oil is added to this mixture. The mixture thus obtained is stirred and heated until fully uniform. This mixture remains stable and liquid at room temperature.

The composition thus obtained is then injected subcutaneously. The injection is performed in the dorsal area, using a conventional syringe for subcutaneous injection. After 2 hours, the animal is sacrificed and a gel is extracted from the site of injection, demonstrating the in vivo formation of the organogel.

EXAMPLE 2

In Vivo Formation of an Organogel from a Composition in Accordance with the Invention Soybean oil is used as hydrophobic organic solvent in accordance with the invention, and ethanol is used as hydrophilic organic solvent according to the invention.

The organogelling substance chosen is LAM (N-lauroyl-L-alanine methyl ester).

The proportions used are summarized in the following table:

| Product | Function | Proportion |
| --- | --- | --- |
| LAM | Organogelling agent | 30% w/v |
| Soybean oil | Hydrophobic organic solvent | qs 100 ml |
| Ethanol | Hydrophilic organic solvent | 18% v/v |

The injection process is identical to that of Example 1, as is the appearance of an organogel 2 h 30 minutes after injection.

EXAMPLE 3

Manufacture of a Composition According to the Invention Containing FITC-Dextran

This composition allows the in vitro measurement of the gradual release of an active substance contained in a preformed organogel.

FITC-dextran is used as active principle, which will allow, by assaying the combined fluorescence, the amount of dextran released by the organogel in accordance with the invention to be measured.

See FIG. 8.

Each point represents the mean value +/−sd (n=3). The area of gel exposed was 0.64 mm².

| Product | Function | Proportion |
| --- | --- | --- |
| FITC-dextran | Active substance | 1.3% p/p |
| LAM | Organogelling agent | 30% w/v |
| Soybean oil | Hydrophobic organic solvent | qs 100 ml |

The LAM is first hot-dissolved in the soybean oil. Next, the FITC-dextran is hot-dispersed in the organic phase formed, after having first ground it using a mortar, until a homogeneous liquid composition is obtained.

This liquid mixture is then introduced gelled by cooling in a test tube. An aqueous saline solution of phosphate-buffered saline is added to the gel.

Samples of the liquid surrounding the organogel in accordance with the invention are then taken over a period of 20 days. The fluorescence emitted by these samples may then be assayed and may thus confirm the sustained release of the FITC-dextran into the surrounding medium. In the event that such a gel is administered in vivo and in accordance with the present invention, an organic solvent of the type such as ethanol should be added so as to inhibit the gelation process before the injection.

The results of this assay are summarized in FIG. 8.

EXAMPLE 4

In Vivo Demonstration of the Hysteretic Properties of an Organogel in Accordance with the Invention. Example of Gelation without a Hydrophilic Solvent The organogelling solution is prepared from the following constituents:

| Product | Function | Proportion |
| --- | --- | --- |
| LAM | Organogelling agent | 40% w/v |
| Benzylbenzoate/ 5% benzyl alcohol | Hydrophobic organic solvent | qs 100 ml |

The hysteretic properties of this organogel were determined beforehand so that the liquid/gel transition temperature is less than 30° C. and the gel/liquid transition temperature is greater than 37° C.

The organogelling solution is first brought to the liquid state by heating, and a volume of 180 μl of this solution cooled to room temperature is then injected subcutaneously into a rat. Once the injection is complete, a compress at 4° C. is applied to the site of injection for 3 minutes, in order to lower the temperature thereof and to bring about gelation.

The animal is sacrificed 2 hours 30 minutes after the injection and a visual observation of the form of the implant is made. The implant is then extracted from the site of injection and weighed.

In this experiment, the implant had a discoid shape about 1 cm in diameter and a weight of 130 mg.

EXAMPLE 5

Formation of an Organogel In Vivo from a Matrix Consisting of a Mixture of Hydrophobic Organic Solvents In this example, it is desired to check the capacity of the organogelling agent to gel in vivo an organogel consisting of a mixture of hydrophobic organic solvents. The tests are performed in rats.

Hydrophobic organic solvents in accordance with the invention are used: soybean oil and ethyl oleate and ethanol as hydrophilic solvent.

The organogelling substance chosen is LAM (N-lauroyl L-alanine methyl ester).

The bioactive substance chosen is leuprolide acetate. An aqueous solution of Leuprolide acetate at 0.67% w/v is made in a first stage.

The proportions used are summarized in the following table:

| Product | Function | Proportion |
| --- | --- | --- |
| LAM | Organogelling agent | 20% w/v |
| Ethanol | Hydrophilic organic solvent | 12% v/v |
| 0.67% w/v solution of leuprolide acetate | Dispersed phase containing the bioactive substance | 8% v/v |
| Soybean oil/ethyl oleate (50/50 v/v) | Hydrophobic organic solvent | qs 100 ml |

The organogelling agent is first dissolved in a warm mixture of soybean oil and ethyl oleate. Next, the ethanol is added to this mixture. The mixture thus obtained is stirred and heated until fully homogenized. This mixture remains stable and liquid at room temperature. Leuprolide acetate is dissolved in distilled water and then added to the liquid mixture. This mixture is stirred and then emulsified by ultra-sonication for two minutes.

Figure 9:
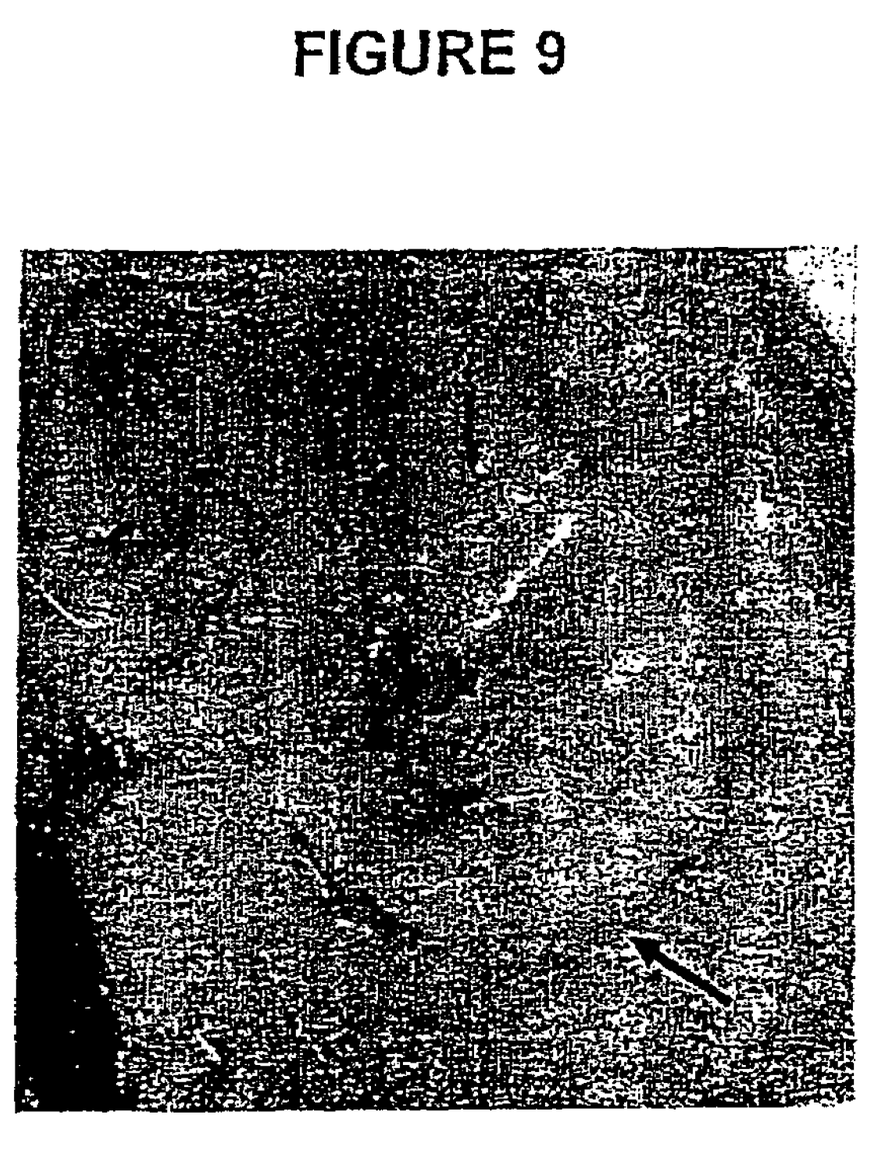
FIG. 9 is a photograph of an implant in accordance with Example 5, at the site of injection.

The composition thus obtained is then injected subcutaneously. The injection is performed into the dorsal area of the rat using a conventional syringe for subcutaneous injection. After 2 hours, the animal is sacrificed and a gel is extracted from the site of injection, demonstrating the in vivo formation of the organogel consisting of a mixture of hydrophobic organic solvents. FIG. 9 shows the form of the implant, obtained according to the composition described in this example, at the site of injection.

EXAMPLE 6

Formation of an Emulsion Containing a Bioactive Substance to be Included into the Composition in Accordance with the Invention It is sought to design a water-in-oil (W/O) stable emulsion that contains a hydrophilic bioactive substance such as leuprolide acetate dissolved in the aqueous phase (dispersed phase).

The bioactive substance chosen is leuprolide acetate. It is dissolved in water in a proportion of 7.62% w/v.

The emulsion is stabilized with two surfactants, polysorbate 20 (Tween 20) and sorbitan trioleate (Span 85), the proportion of each of which is adjusted as a function of the hydrophilic/hydrophobic balance of the emulsion to be designed.

The proportions used are summarized in the following table:

| Product | Proportion (v/v) |
| --- | --- |
| 7.62% w/v solution of leuprolide acetate | 12.2% |
| 10% w/v solution of Tween 20 in water | 7.8% |
| 10% w/v solution of Span 85 in soybean oil | 2.2% |
| Soybean oil | 77.8% |

A 10% w/v solution of Span 85 in soybean oil and a 10% w/v solution of Tween 20 in water are prepared. The various phases are then combined and the mixture is stirred and heated until fully homogenized. This mixture remains stable and liquid at room temperature and may be added directly to a mixture of oils, organogelling agent and N,N-dimethylacetamide (DMAc) (see Example 7).

EXAMPLE 7

Formation of an Organogel In Vitro Using a Composition Containing an Emulsion and a Hydrophilic Organic Solvent other than Ethanol In this example, it is sought to check the capacity of a hydrophilic organic solvent other than ethanol to inhibit the gelation of the organogel at room temperature.

Soybean oil is used as hydrophobic organic solvent and N,N-dimethylacetamide (DMAc) is used as hydrophilic organic solvent.

The organogelling substance chosen is LAM (N-lauroyl L-alanine methyl ester).

The proportions used are summarized in the following table:

| Product | Function | Proportion |
| --- | --- | --- |
| LAM | Organogelling agent | 18.4% w/v |
| N,N-dimethyl-acetamide | Hydrophilic organic solvent | 18.4% v/v |
| W/O emulsion | Vehicle for the bioactive substance | 8.2% v/v |
| Soybean oil | Hydrophobic organic solvent | qs 100 ml |

The organogelling agent is first dissolved in warm soybean oil. Next, the DMAc is added to this mixture. The mixture thus obtained is stirred and heated, the emulsion is then added and the mixture is stirred until fully homogenized. This mixture remains stable, and is viscous at room temperature (similar to a cream) and may be injected in this form using a conventional syringe subcutaneously. The gel forms after injection of this viscous preparation.

The invention claimed is:

1. A heat-sensitive composition in liquid form, comprising a hydrophobic organic liquid,
   an organogelling substance selected from the group consisting of N-lauroyl-L-alanine methyl ester, N-lauroyl-L-alanine ethyl ester, N-stearoyl-L-alanine methyl ester and N-stearoyl-L-alanine ethyl ester, the molecules of which have the capacity to bind together via bonds of low energy, and
   a bioactive substance,
   wherein the composition changes from a liquid to a gel form after its administration to an animal body and remains in gel form at the body temperature of said animal body and said gel form has a gel/liquid transition temperature that is higher than the liquid/gel transition temperature.

2. The composition according to claim 1, further comprising a hydrophilic organic solvent capable of creating weak bonds with the organogelling substance.

3. The composition according to claim 1 wherein said gel form has a transition temperature from the liquid state to the gel state which is lower than the temperature of the site of application, and a transition temperature from the gel state to the liquid state that is higher than the body temperature.

4. The composition according to claim 3, wherein said gel form has a transition temperature from the liquid state to the gel state of less than 30° C. and a transition temperature from the gel state to the liquid state of greater than +35° C.

5. The composition according to claim 2, wherein the proportion of the hydrophilic organic solvent is less than 60% by weight of said composition.

6. The composition according to claim 2, wherein said hydrophilic organic solvent is selected from the group consisting of ethanol, glycerol, benzyl alcohol, propylene glycol, N-methylpyrrolidone, dimethyl sulphoxide (DMSO), poly(ethylene) glycol of low molecular weight, chlorobutanol, furfural, N,N-dimethylacetamide, glycerol formal, isopropylideneglycerol, ethyl lactate, acetic acid and lactic acid.

7. The composition according to claim 6, wherein said hydrophilic organic solvent is ethanol.

8. The composition according to claim 1, wherein said hydrophobic organic liquid is selected from the group consisting of plant oils, triglycerides, semi-synthetic oils and water-immiscible organic solvents.

9. The composition according to claim 8, wherein said hydrophobic organic liquid is selected from the group consisting of soybean oil, squalene, benzyl benzoate, a triglyceride or a mixture of benzyl benzoate and benzyl alcohol.

10. The composition according to claim 8, wherein said hydrophobic organic liquid is a mixture of different hydrophobic organic solvents.

11. The composition according to claim 10, wherein said hydrophobic organic liquid is a mixture of soybean oil and ethyl oleate.

12. The composition according to claim 1, wherein said bioactive substance is selected from the group consisting of proteins, peptides, amino acids, vitamins, nucleic acids and oligonucleotides.

13. The composition according to claim 1, wherein said bioactive substance is selected from the group consisting of morphine, α-interferon, β-interferon, somatostatin, heparin, interleukins, erythropoietin, calcitonin, human growth hormone, thyreotrope hormone and leuprolide.

14. The composition according to claim 1, wherein the organogelling substance represents between 0.5% and 50% by weight relative to the total weight of said composition.

15. An organogel formed from the composition according to claim 1, which is capable of remaining stable in gelled form between the temperature of application and the gel/liquid transition temperature of said composition.

16. A method for administering a bioactive substance to an animal comprising injecting the composition according to claim 1 into the body of said animal via the extravascular parenteral route, the intraocular route or the vaginal route, to an open wound or during surgery.

17. A process for preparing a composition according to claim 1, wherein the bioactive substance, optionally in aqueous solution, is added to a mixture comprising the organogelling substance and the hydrophobic organic liquid.

18. The composition according to claim 5, wherein the proportion of the hydrophilic organic solvent is less than 20% by weight of said composition.

19. The composition according to claim 9, wherein said hydrophobic organic liquid is a mixture of different hydrophobic organic solvents.

20. The composition according to claim 1, wherein said organogelling substance is N-lauroyl-L-alanine methyl ester or N-lauroyl-L-alanine ethyl ester.

21. The composition according to claim 1, wherein said organogelling substance is N-stearoyl-L-alanine methyl ester or N-stearoyl-L-alanine ethyl ester.

22. The method according to claim 16, wherein said composition is injected into the body of said animal via the subcutaneous route, the intradermal route, the intraperitoneal route or the intramuscular route.

23. A method for delivering a bioactive substance into an animal body for the sustained release of said bioactive substance therefrom, comprising administering said bioactive substance into said body in the form of a composition according to claim 1.

24. The method according to claim 16, wherein the animal is a human.

25. The method according to claim 23, wherein the animal body is a human body.

26. The composition according to claim 1, wherein the organogelling substance is N-lauroyl-L-alanine methyl ester.

27. The method of claim 16, wherein the temperature at the site of injection is cooled below the liquid to gel transition temperature.

28. The method of claim 23, wherein the temperature at the site of injection is cooled below the liquid to gel transition temperature.

* * * * *